United States Patent
Orozco et al.

(10) Patent No.: US 11,633,255 B2
(45) Date of Patent: Apr. 25, 2023

(54) HIGH DEFINITION STABILIZED CAMERA SYSTEM FOR OPERATING ROOMS

(71) Applicant: Sunoptic Technologies LLC, Jacksonville, FL (US)

(72) Inventors: Walter Orozco, Jacksonville, FL (US); Frank Robson, Middleburg, FL (US); Brandon Closson, St. Johns, FL (US)

(73) Assignee: SUNOPTIC TECHNOLOGIES LLC, Jacksonville, FL (US)

( * ) Notice: Subject to any disclaimer, the term of this patent is extended or adjusted under 35 U.S.C. 154(b) by 78 days.

(21) Appl. No.: 17/036,614

(22) Filed: Sep. 29, 2020

(65) Prior Publication Data

US 2021/0093416 A1 Apr. 1, 2021

Related U.S. Application Data

(60) Provisional application No. 62/908,005, filed on Sep. 30, 2019.

(51) Int. Cl.
*A61B 90/00* (2016.01)
*G03B 15/14* (2021.01)

(52) U.S. Cl.
CPC ............ *A61B 90/361* (2016.02); *G03B 15/14* (2013.01); *A61B 2090/3614* (2016.02)

(58) Field of Classification Search
CPC .......... A61B 90/361; A61B 2090/3614; A61B 2017/00199; A61B 2090/373; A61B 90/30; A61B 2090/502; A61B 2090/306; G03B 15/14; G03B 3/00; G03B 5/00; G03B 2215/05
USPC ..................................... 348/77, 125
See application file for complete search history.

(56) References Cited

U.S. PATENT DOCUMENTS

| | | | | |
|---|---|---|---|---|
| 6,122,045 | A * | 9/2000 | Pike ...................... | G01B 11/105 348/125 |
| 2002/0021869 | A1* | 2/2002 | Griffin .................. | A61B 5/0075 385/31 |
| 2005/0071166 | A1* | 3/2005 | Comerford ............. | G10L 15/25 704/E15.042 |
| 2016/0287211 | A1* | 10/2016 | DaCosta .................. | A61B 8/48 |
| 2018/0020920 | A1* | 1/2018 | Ermilov ............... | A61B 5/0095 600/317 |
| 2018/0316834 | A1* | 11/2018 | Grabow ............... | H04N 5/2253 |
| 2019/0086066 | A1* | 3/2019 | Boesen ..................... | F21V 7/06 |
| 2019/0331592 | A1* | 10/2019 | Dighe ................. | G03F 7/70616 |
| 2020/0337776 | A1* | 10/2020 | Saun ..................... | H04N 5/765 |

* cited by examiner

*Primary Examiner* — Thai Q Tran
*Assistant Examiner* — Stephen R Smith
(74) *Attorney, Agent, or Firm* — Howson & Howson LLP

(57) ABSTRACT

An image capturing and illumination system comprises a headband, a camera head mounted on the headband and having a camera lens defining a focal point, and a fiber-optic lens assembly for transmitting light therefrom. The fiber-optic lens assembly includes a pair of laterally spaced-apart lenses flanked on opposite sides of the camera lens for directing beams of light toward the focal point.

4 Claims, 3 Drawing Sheets

HIGH DEFINITION STABILIZED CAMERA SYSTEM FOR OPERATING ROOMS

CROSS REFERENCE TO RELATED APPLICATIONS

This application claims the benefit under 35 USC § 119(e) of U.S. Provisional Patent Application No. 62/908,005 filed Sep. 30, 2019.

BACKGROUND

The present invention relates to a surgical headlight that provides illumination to a surgeon's area of work, and specifically to a surgical headlight and camera that allows for recording images and/or video of the surgical area during an operation as seen from the surgeon's perspective and line of sight.

When still or moving images (digital or otherwise) of a surgery need to be captured, recorded, or streamed in a typical hospital environment, video camera recording is generally accomplished with a coaxial camera system in which a camera lens is substantially aligned with a light beam along a centerline of the light beam. Such systems typically produce relatively unsteady and shaky video recordings of a low quality and at a low resolution which can make it difficult to properly visualize important aspects of the captured video during playback and review, and the light and camera angle are typically poorly aligned.

Additionally, the camera of the system is typically mounted in front of the headlight lens which necessarily obstructs light being projected from the headlight and reduces illumination of the surgical site. The light is typically delivered by a single elongate fiber optic cable which connects to a headlight at the front of the headband and can cause the headband to pull in whatever direction the cable is routed to the headband from an illuminator. Further, these systems typically require a monitor for the system to be functional, as the system itself does not typically have a screen that can be used in real-time to control the recording system during image capture.

SUMMARY

According to the present development, an image capturing and illumination system comprises a headband, a camera head mounted on the headband and having a camera lens defining a focal point, and a fiber-optic lens assembly for transmitting light therefrom. The fiber-optic lens assembly includes a pair of laterally spaced-apart lenses flanked on opposite sides of the camera lens for directing beams of light from opposite sides of the camera lens toward the focal point of the camera lens.

According to another aspect of the present development, a modular image capturing and illumination system comprises a headband having a camera head mounted thereon with a camera lens defining a focal point and a fiber-optic lens assembly for transmitting light therefrom. The fiber-optic lens assembly includes a pair of laterally spaced-apart lenses flanked on opposite sides of the camera lens for directing beams of light at the focal point. The system also includes a camera control system that receives data from the camera head of images captured by via the camera lens. The camera control system provides image stabilization in real-time to the video stream of data received from the camera head.

BRIEF DESCRIPTION OF THE DRAWINGS

The features and advantages of the present invention should become apparent from the following description when taken in conjunction with the accompanying drawings, in which.

DETAILED DESCRIPTION

Figure 1:
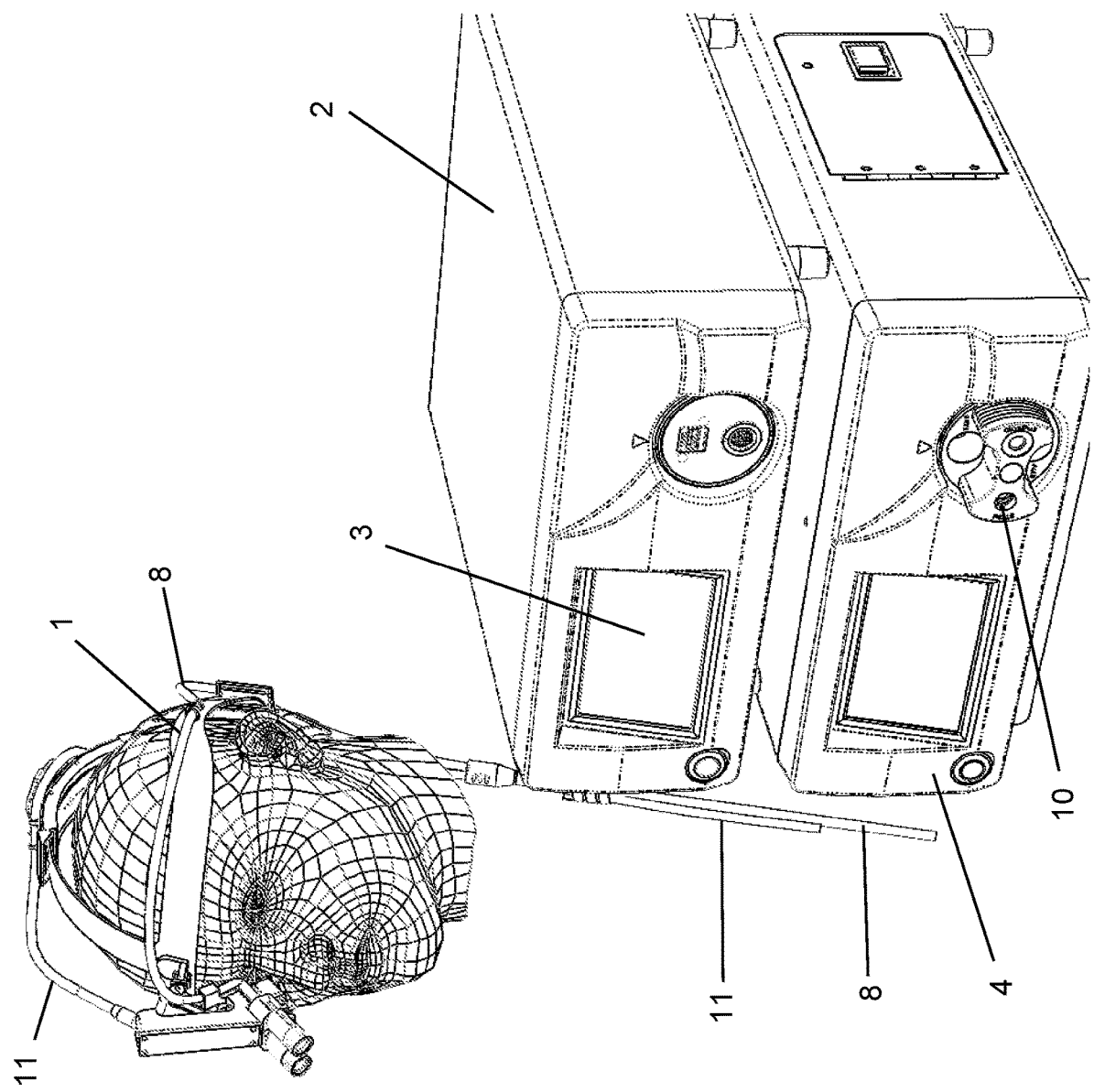
FIG. 1 is a perspective view of image capturing apparatus according to an embodiment.

According to an embodiment, a camera lens for capturing an image is flanked by a dual light-emitting fiber-optic lens setup that centers with a focal point or length of the camera lens at an industry standard distance at which the subject matter of interest being imaged is in focus in an image being captured by the camera system. The focal point is also the same point the eyes of the surgeon are focused on during a surgery or like procedure. The focal point of the camera and location of the spotlight produced by the dual light-emitting fiber-optic lens may be adjustable and customizable, such as to accommodate the working distances of surgeons of different heights. Thus, the dual light-emitting fiber-optic lens arrangement centers a spotlight on the surgical site without undue light loss caused by interfering structures or camera lenses.

Accordingly, with use of the above referenced so-called "prismatic" technique, instead of a conventional coaxial technique (in which the camera lens and light beam share a common centerline) discussed above, the user of the image capturing system is provided with a cleaner, brighter illumination spot at the point of interest because the camera head is not positioned directly in front of the light-emitting lens or source and does not limit the amount of light reaching the point of interest. Accordingly, the camera lens is prismatically aimed and focused on the center of the light spot for clear image capture, such as 1080p resolution image capture.

The dual fiber-optic light-emitting lens setup may be connected to a separate standard light source or illuminator using a bifurcated fiber-optic cable instead of a typical single output cable. This permits light from the same light source to be split and transmitted to both fiber-optic lenses and permits the bifurcated fiber-optic cable to extend to the rear of the headband worn by the surgeon so that the cable does not pull to one side of the headband or the other during use.

Such an image capturing system may also include a digital touch screen on the front of a control unit to provide the user with significant control over system operation, such as camera operations and customizable image settings. Such settings may be savable and readily retrievable via the image capturing system. In addition, a full keyboard (not shown) can be attached to the unit, allowing the user to enter patient information, delete files, and have greater access to the functionality of the memory system within the device. Alternatively, the system may provide an on-screen keyboard or the like. Further, the system may include a foot controller or pedal enabling additional image capture controls.

Still further, the system may provide user-switchable video outputs and live image stabilization in real-time of the image or video being captured, recorded on internal media, or streamed to a local area network and output or stored by the system for reducing image jitter during display or replay of the video caused by sudden or frequent movements of the surgeon while the video is being captured. The software of the system able to provide the above functions may have field-update capabilities and the system may be assembled in a modular manner providing the user with various features, such as camera-only operation, recording and playback, and live image stabilization.

Thus, embodiments disclosed herein provide a fully functional modular camera system that includes a headband having a combination headlight and camera head assembly attached thereto and a camera control system having a memory or storage device and camera control unit (CCU) that controls recording, file maintenance, and output functions and options. A separate light source or fiber-optic illuminator may be included and connected to the headlight via a cable or the like for purposes of illuminating a surgical site or the like.

According to an embodiment as shown in FIG. 1, an image capturing system may include a camera headband assembly 1 for being worn on the head of a surgeon or the like, a camera control system unit 2 having a digital touch screen 3, and a light source or illuminator unit 4 having a fiber-optic light-beam output connection port 10. Although not completely shown in FIG. 1, a video cable 11 may extend from the camera headband assembly 1 to the camera control system unit 2 and a fiber-optic light-transmitting cable 8 may extend from the camera headband assembly 1 to the port 10 of the light source unit 4. Alternatively, data may be streamed via a wireless connection from the camera headband assembly to the camera control system unit 2 and/or the light source unit 4 may be replaced with a portable light source carried on the camera headband assembly 1.

Figure 2:
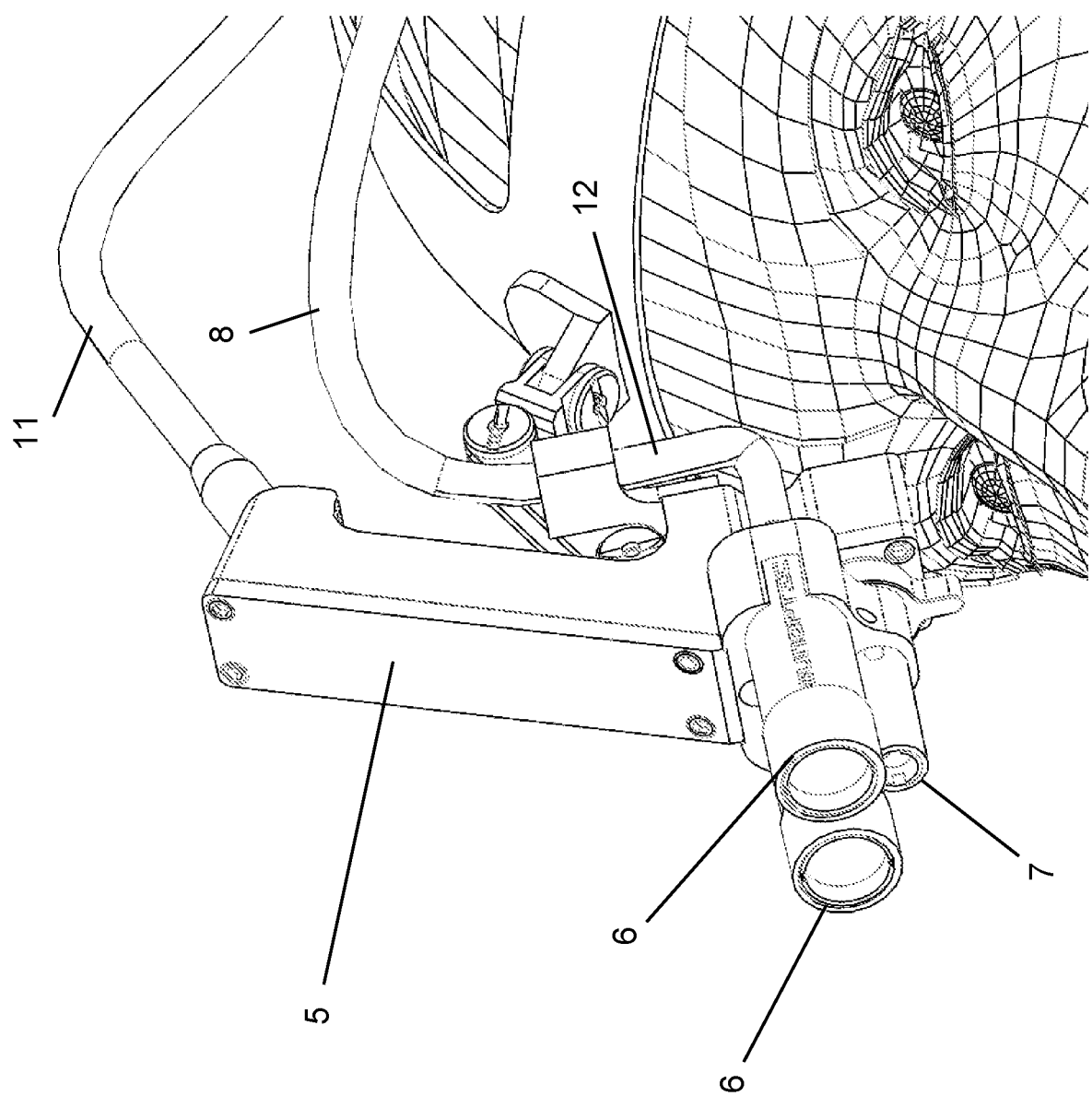
FIG. 2 is a perspective view of a camera unit of the imaging capturing apparatus of FIG. 1 mounted on a forehead of a surgeon in accordance with an embodiment.

As best shown in FIG. 2, the camera headband assembly 1 includes a camera head 5, a fiber-optic lens assembly 6 from which light is projected, a fiber optic cable 8 for transferring light from the light source unit 4 to the fiber-optic lens assembly 6, and a camera lens 7 from which images and video is captured by the camera head 5. As shown in FIG. 2, the fiber-optic lens assembly 6 includes a pair of lenses from which light is projected from the camera headband assembly 1. The cable 8 may be a single cable 8 that connects to the light source unit 4 and that has a bifurcated end 12 enabling the cable 8 to be connected to and transmit light to both fiber-optic lenses of the assembly 6.

Figure 3:
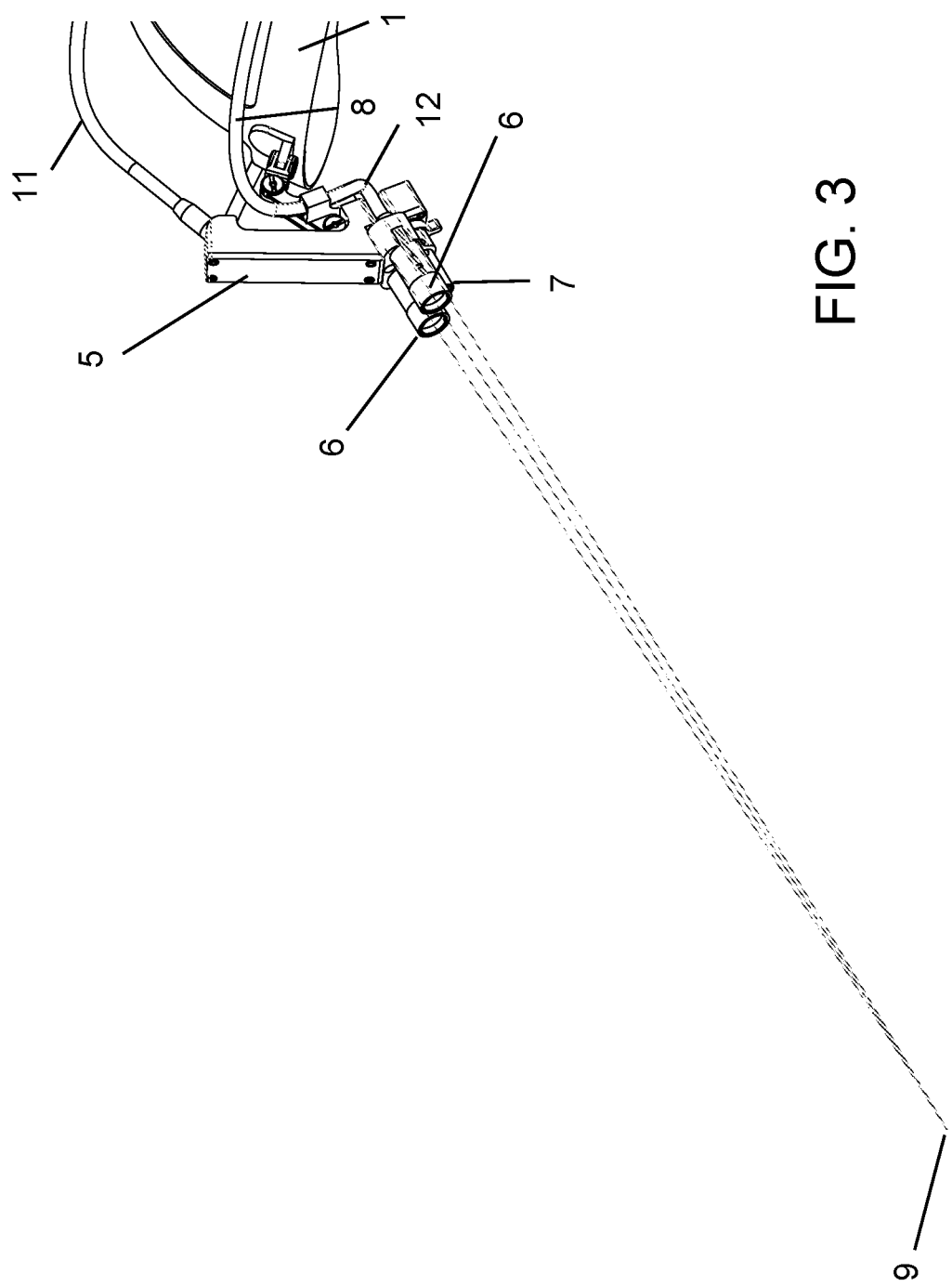
FIG. 3 is a perspective view showing a focal point of the camera unit relative to the centerlines of a pair of beams of light being emitted from a headlight of the imaging capturing apparatus of FIG. 1 in accordance with an embodiment.

According to an embodiment, the lenses of the fiber-optic lens assembly 6 may be laterally spaced-apart a sufficient distance to permit the camera lens 7 of the camera head 5 to extend therebetween. Thus, the camera lens 7 is closely flanked on both sides thereof by one of the lenses of the fiber-optic lens assembly 6. The spacing of the camera lens 7 relative to the lenses of the fiber-optic lens assembly 6 is such that the camera lens 7 does not reduce the amount of light being projected to a point of interest being recorded by the camera lens 7 and such that the lenses of the fiber-optic lens assembly 6 do not appear in the image being recorded via the camera lens 7. As best shown in FIGS. 2 and 3, the fiber-optic lens assembly 6 may extend forwardly of the camera lens 7.

As shown in FIG. 3, a focal point 9 is located a spaced distance in front of the camera lens 7 that corresponds to the point of interest of the matter being recorded via the camera lens. The focal point 9 defines a point at a distance from the camera lens 7 at which the subject matter of interest being imaged is in focus in an image being captured by the camera head 4. This distance may be adjusted or customized. Each of the lenses of the fiber-optic lens assembly 6 is positioned to direct a beam of light along a centerline which crosses the focal point 9 of the camera lens 7. Thus, the beams of light from the lenses of the fiber-optic lens assembly 6 are aligned such that they cross at the focal point 9. This "prismatic" alignment is illustrated for the fiber-optic lens assembly 6 and the camera lens 7 in FIG. 3. This "prismatic" headlight design having two barrels or lenses via which a pair of light beams are focused and directed provides a targeted maximum illumination at the center of the intended image location being recorded by the camera head 4 via the camera lens 7.

According to other aspects of an embodiment, the camera system may apply live stabilization to the data of the video stream to correct unstable or shaky images and may produce images having at least 1080p high definition resolution. In addition, the system can be provided with a modular design thereby allowing other features to be added to or removed from the system, for instance, 4k, zoom, stabilization, white balance, and like features of desire.

While a preferred image capturing system has been described in detail, various modifications, alternations, and changes may be made without departing from the spirit and scope of the system according to the present invention as defined in the appended claims.

The invention claimed is:

1. An image capturing and illumination system, comprising:
   a headband;
   a camera head mounted on the headband and having a camera lens defining a focal point;
   a fiber-optic lens assembly for transmitting light therefrom, said fiber optic lens assembly including a pair of laterally spaced-apart lenses flanked on opposite sides of said camera lens for directing beams of light at said focal point, each of said pair of laterally spaced-apart lenses being arranged to direct a beam of light defining a longitudinally extending centerline thereof such that said centerlines cross at said focal point of said camera lens, and each of said pair of laterally spaced-apart lenses of said fiber optic lens assembly extending forward of said camera lens relative to said focal point;
   a fiber-optic cable having a bifurcated end that connects to said fiber-optic lens assembly;
   a light source that connects to said fiber-optic cable for transmitting light to said fiber-optic lens assembly; and
   a camera control system that receives data from said camera head of images captured via said camera lens;
   wherein said camera control system is adapted to provide image stabilization in real-time to a video stream of data received from said camera head.

2. The system according to claim 1, further comprising a video cable that connects said camera head to said camera control system.

3. The system according to claim 1, wherein said camera control system includes a touch screen.

4. The system according to claim 1, wherein said camera head captures images of at least 1080p high definition resolution.

* * * * *